US010446266B1

(12) United States Patent
Daniel et al.

(10) Patent No.: US 10,446,266 B1
(45) Date of Patent: Oct. 15, 2019

(54) SYSTEM AND METHOD FOR OPTIMIZING NUCLEAR IMAGING APPROPRIATENESS DECISIONS

(71) Applicant: Emerge Clinical Solutions, LLC, Dallas, TX (US)

(72) Inventors: William C Daniel, Overland Park, KS (US); David Yaron, Haifa (IL); Scott Finfer, Dallas, TX (US); Efrat Erps, Givatayim (IL)

(73) Assignee: Emerge Clinical Solutions, LLC, Dallas, TX (US)

(*) Notice: Subject to any disclaimer, the term of this patent is extended or adjusted under 35 U.S.C. 154(b) by 503 days.

(21) Appl. No.: 15/356,179

(22) Filed: Nov. 18, 2016

Related U.S. Application Data

(63) Continuation-in-part of application No. 13/627,031, filed on Sep. 26, 2012, now abandoned.

(60) Provisional application No. 61/542,717, filed on Oct. 3, 2011.

(51) Int. Cl.

| | |
|---|---|
| *G16H 10/60* | (2018.01) |
| *G06F 19/00* | (2018.01) |
| *A61B 5/00* | (2006.01) |
| *A61B 6/12* | (2006.01) |
| *A61B 6/00* | (2006.01) |
| *A61B 34/10* | (2016.01) |
| *G16H 50/30* | (2018.01) |

(52) U.S. Cl.
CPC ........... *G16H 10/60* (2018.01); *A61B 5/7275* (2013.01); *A61B 6/12* (2013.01); *A61B 6/4258* (2013.01); *A61B 6/503* (2013.01); *A61B 6/504* (2013.01); *A61B 6/507* (2013.01); *A61B 6/5217* (2013.01); *A61B 6/563* (2013.01); *A61B 34/10* (2016.02); *G06F 19/321* (2013.01); *G16H 50/30* (2018.01)

(58) Field of Classification Search
None
See application file for complete search history.

(56) References Cited

U.S. PATENT DOCUMENTS

| | | | | |
|---|---|---|---|---|
| 2001/0050610 | A1* | 12/2001 | Gelston | G16H 40/20 340/5.53 |
| 2002/0019749 | A1* | 2/2002 | Becker | G06F 19/325 705/2 |

OTHER PUBLICATIONS

Brindis RG, Douglas PS, Hendel RC, Peterson ED, Wolk MJ, Allen JM, Patel MR, Raskin IE. ACCF/ASNC appropriateness criteria for single-photon emission computed tomography myocardial perfusion imaging (SPECT MPI), JACC vol. 46, No. 8, 2005, 1587-1605.*

(Continued)

*Primary Examiner* — Michael Tomaszewski
(74) *Attorney, Agent, or Firm* — William H. Quirk; Jesse Frizzell; Rosenthal Pauerstein Sandoloski Agather LLP

(57) ABSTRACT

Methods and systems of accelerating the adoption of a medical treatment by healthcare providers are disclosed. The methods include providing to a healthcare provider a set of selectable criteria for determining whether a specific medical treatment is indicated for a particular patient, analyzing the criteria selected, and indicating to the healthcare provider whether the medical treatment is indicated. A system and methods are provided which are suitable for optimizing the use of nuclear imaging for assessing risks of cardiovascular disorders and, when appropriate, for implementing intervention strategies to reduce such risks.

14 Claims, 6 Drawing Sheets

(56) References Cited

OTHER PUBLICATIONS

Hendel RC, Berman DS, Di Carli MF, Heidenreich PA, Henkin RE, Pellikka PA, Pohost GM, Williams KA. ACCF/ASNC/ACR/AHA/ASE/ SCCT/SCMR/SNM 2009 appropriate use criteria for cardiac radionuclide imaging, JACC vol. 53, No. 23, 2009, 2201-2229.*
Practice Guidelines AHA and ACC Outline Approaches to Coronary Disease Risk Assessment; Sharon Scott Morey Am Fam Physician. Apr. 15, 2000;61 (8):2534-2542.; www.aafp.org/afp/2000/0415/p2534.html?printable=afp.*

* cited by examiner

| Framingham Risk | 30 year risk of cardiovascular disease |
|---|---|
| Risk level | Risk Percentage |
| Low | less than 10 |
| Moderate | between 10 and 20 |
| High | greater than 20 |

Total points are the sum of Age Points, HDL Points, Smoking Points, Blood Pressure Points, and Total Chol Points

Men

| Risk Percentage | Total points |
|---|---|
| less than 1% | less than 0 |
| 1% | between 0 and 4 |
| 2% | 5 |
| 5% | 6 |
| 7% | 7 |
| 8% | 8 |
| 10% | 9 |
| 13% | 10 |
| 16% | 11 |
| 20% | 12 |
| 25% | 13 |
| 31% | 14 |
| 37% | 15 |
| 45% | 16 |
| greater than 45% | more than 16 |

Age Points

| Age | Age points |
|---|---|
| less than 35 | -9 |
| 35-39 | -4 |
| 40-44 | 0 |
| 45-49 | 3 |
| 50-54 | 6 |
| 55-59 | 8 |
| 60-64 | 10 |
| 65-69 | 11 |
| 70-74 | 12 |
| more than 74 | 13 |

HDL Points

| HDL | HDL Points |
|---|---|
| less than 40 | 2 |
| 40-49 | 1 |
| 50-59 | 0 |
| more than 59 | -1 |

Smoking Points

| | Smoking points |
|---|---|
| Non-smoker | 0 |
| Smoker age | |
| less than 40 | 8 |
| 40-49 | 5 |
| 50-59 | 3 |
| 60-69 | 1 |
| 70-79 | 1 |
| 80+ | 0 |

Blood Pressure Points

| Systolic BP/HTN treated | Blood Pressure Points |
|---|---|
| Systolic BP less than 120 | 0 |
| 120-129/treated | 1 |
| 120-129/not treated | 0 |
| 130-139/treated | 2 |
| 130-139/not treated | 1 |
| 140-159/treated | 2 |
| 140-159/not treated | 1 |
| 160 or more/treated | 3 |
| 160 or more/not treated | 2 |

Total Chol Points

| | Total Chol Points |
|---|---|
| Total Chol < 160 or age 80+ | 0 |
| Total Chol 160-199 | |
| Age < 40 | 4 |
| Age 40-49 | 3 |
| Age 50-59 | 2 |
| Age 60-69 | 1 |
| Age 70-79 | 1 |
| Total Chol 200-239 | |
| Age < 40 | 7 |
| Age 40-49 | 5 |
| Age 50-59 | 3 |
| Age 60-69 | 1 |
| Age 70-79 | 0 |
| Total Chol 240-279 | |
| Age < 40 | 9 |
| Age 40-49 | 6 |
| Age 50-59 | 4 |
| Age 60-69 | 2 |
| Age 70-79 | 1 |
| Total Chol > 279 | |
| Age < 40 | 11 |
| Age 40-49 | 8 |
| Age 50-59 | 5 |
| Age 60-69 | 3 |
| Age 70-79 | 1 |

Women

| Risk Percentage | Total points |
|---|---|
| less than 1% | less than 9 |
| 1% | between 9 and 12 |
| 2% | 13 or 14 |
| 3% | 15 |
| 4% | 16 |
| 5% | 17 |
| 6% | 18 |
| 8% | 19 |
| 11% | 20 |
| 14% | 21 |
| 17% | 22 |
| 22% | 23 |
| 27% | 24 |
| greater than 30% | more than 24 |

Age Points

| Age | Age points |
|---|---|
| less than 35 | -7 |
| 35-39 | -3 |
| 40-44 | 0 |
| 45-49 | 3 |
| 50-54 | 6 |
| 55-59 | 8 |
| 60-64 | 10 |
| 65-69 | 12 |
| 70-74 | 14 |
| more than 74 | 16 |

HDL Points

| HDL | HDL Points |
|---|---|
| less than 40 | 2 |
| 40-49 | 1 |
| 50-59 | 0 |
| more than 59 | -1 |

Smoking Points

| | Smoking points |
|---|---|
| Non-smoker | 0 |
| Smoker age | |
| less than 40 | 9 |
| 40-49 | 7 |
| 50-59 | 4 |
| 60-69 | 2 |
| 70-79 | 1 |
| 80+ | 0 |

Blood Pressure Points

| Systolic BP/HTN treated | Blood Pressure Points |
|---|---|
| Systolic BP less than 120 | 0 |
| 120-129/treated | 2 |
| 120-129/not treated | 1 |
| 130-139/treated | 4 |
| 130-139/not treated | 2 |
| 140-159/treated | 5 |
| 140-159/not treated | 3 |
| 160 or more/treated | 6 |
| 160 or more/not treated | 4 |

Total Chol Points

| | Total Chol Points |
|---|---|
| Total Chol < 160 or age 80+ | 0 |
| Total Chol 160-199 | |
| Age < 40 | 4 |
| Age 40-49 | 3 |
| Age 50-59 | 2 |
| Age 60-69 | 1 |
| Age 70-79 | 1 |
| Total Chol 200-239 | |
| Age < 40 | 8 |
| Age 40-49 | 6 |
| Age 50-59 | 4 |
| Age 60-69 | 2 |
| Age 70-79 | 1 |
| Total Chol 240-279 | |
| Age < 40 | 11 |
| Age 40-49 | 8 |
| Age 50-59 | 5 |
| Age 60-69 | 3 |
| Age 70-79 | 2 |
| Total Chol > 279 | |
| Age < 40 | 13 |
| Age 40-49 | 10 |
| Age 50-59 | 7 |
| Age 60-69 | 4 |
| Age 70-79 | 2 |

FIG. 2

SYSTEM AND METHOD FOR OPTIMIZING NUCLEAR IMAGING APPROPRIATENESS DECISIONS

CLAIM OF PRIORITY TO PRIOR APPLICATION

This application is a continuation-in-part of prior filed co-pending U.S. Non-Provisional application Ser. No. 13/627,031, filed on Sep. 26, 2012, entitled "System and Method for Optimizing Nuclear Imaging Appropriateness Decisions," which claims the benefit of the filing date of U.S. Provisional Application Ser. No. 61/542,717, filed on Oct. 3, 2011, entitled "System and Method for Optimizing Nuclear Imaging and Appropriateness Decisions." By this reference, the entire disclosures, including the claims and drawings, of prior filed co-pending U.S. Non-Provisional application Ser. No. 13/627,031 and U.S. Provisional Application Ser. No. 61/542,717, are hereby incorporated into the present disclosure as if set forth in their entirety.

NONPUBLICATION REQUESTED—NON PROVISIONAL APPLICATION

This application is a Nonprovisional Application under 37 CFR 1.53(b) and is submitted with an accompanying non-publication request in accordance with 35 CFR U.S.C. § 122(b)(2)(B). Accordingly, the subject matter of this application is to be maintained in secrecy until and unless Applicant allows a patent to issue based on this application.

BACKGROUND OF THE INVENTION

1. Field of the Invention

The present invention relates to the field of healthcare risk management, particularly as it relates to optimizing the use of nuclear imaging for assessing risks of cardiovascular disorders and, when appropriate, for evaluating and implementing intervention strategies to reduce such risks. More particularly, many aspects of the present invention relate to enabling efficient and effective determinations whether the expense of nuclear imaging is likely to be suitable and improving the systems and methods for implementation of appropriate risk assessment procedures for a particular patient.

2. Description of Background and Related Art

Optimal management of healthcare is an incredibly enormous challenge, and the need for more efficient-yet-effective solutions is extremely grave—not just for the healthcare system and its patients—but for the entire United States economy. While Americans hope for a gallant knight to provide miraculous sweeping solutions for the entire system, there remains a huge unmet need for technology to help solve the crisis at every level in healthcare management.

A particular need for better solutions revolves around balancing the costs and benefits of using nuclear imaging for screening purposes. Each nuclear imaging procedure involves substantial expense and involves a level of risk in itself due for instance to radiation exposure, and yet the potential value is also tremendous. If we can capture the right images at the right times for the right patients, then we can accurately determine whether or not, and when, to implement other more costly and/or more invasive interventions in order to avoid still greater expenses and unnecessary loss of life. From a cost management perspective, the challenge is deciding whether and when nuclear imaging is likely to be of more value than the costs.

Thankfully, various scoring systems and the like have been developed as statistically sound predictors for whether more costly procedures such as nuclear imaging are likely to be justified in a particular case. In the cardiovascular field, one of the more widely trusted of these scoring systems is the Framingham Risk Score (FRS, publicized in 1998 and revised at least twice since). FRS can be a fairly reliable identifier of individuals at increased risk for future cardiovascular events, which can be useful in helping decide whether interventions should be implemented to reduce the risks and whether more extensive and costly assessments, such as nuclear imaging, are likely to be beneficial. The costs of nuclear imaging are usually accepted as appropriate if a patient's FRS indicates at least moderate or intermediate risk of cardiovascular disease, whereas nuclear imaging is generally NOT considered appropriate if a patient's FRS indicates a low risk for cardiovascular disorders.

Unfortunately, even though use of FRS and other analogous factors has long been widely encouraged to help appropriately manage nuclear imaging decisions, it is much easier said than done. Despite the reliability of FRS, determining the score itself is a complicated process replete with opportunity for error, particularly if answers are rushed. Too often the data is not available for every factor in the analysis, and the score becomes less accurate and less reliable. Consistent reliable use of FRS for nuclear imaging decisions seems to require ideal situations where time availability is abundant, information systems run perfectly, and healthcare personnel are continually superhuman. The usefulness of such a score can, hence, be frustrated in the moment at the point of care if some of the necessary data is unavailable or if caregivers do not have adequate support to minimize errors. Consequently, routine use of FRS for making nuclear imaging decisions has not been adequately attainable. Although the system demands it, healthcare personnel can't continually know everything at once, and it is very challenging to have a mastery of all known risk factors for a variety of disease conditions, particularly when competing standards are being debated in academia or when the standards themselves are imprecise ideals that are difficult to implement in practice.

Electronic medical record (EMR) systems and Healthcare Information Management Systems (HIMS) have helped on the data retention and retrieval side of the problems by allowing easier access to a patient's historical data, but such systems are not and perhaps can never be intelligent enough to substitute for real time observation by a healthcare practitioner. The SureCare system made available in some facilities has offered rules-based risk assessment processing support for other fields such as heart failure, and other information systems have reportedly been customized in attempts to add a level of predictive processing that raises focused alerts based on a patient's history in the realms of diabetes care and oncology. However, reliably effective implementation has been very challenging even in those other fields.

Seemingly unavoidable practical challenges and systemic limitations have confounded practical and effective use of such scoring systems for optimizing nuclear imaging decisions. Moreover, healthcare administrations are very cautious about minimizing the human professional element out of the risk management decision-making process. Electronic processing systems cannot be made intelligent enough, and the potential liabilities are too great. Human caregivers are flawed enough without adding another layer of uncertainty by delegating decisions to computers. Plus, scoring systems are theoretical and do not always account for real world situations. As a result, prior to the present invention, there has been a long felt need for systems that can consistently and reliably implement risk scoring systems to help in the determination of whether and when to conduct nuclear imaging as a cardiovascular risk management tool.

Moreover, different systems have been developed over the years for creating orders for medical tests or procedures, inserting such orders into a hospital or clinic system, and implementing such orders. Many such ordering systems have been developed such that order generation and insertion can be accomplished, at least in part, through a computer-based functionality.

In addition, at least some medical procedures require prior authorization before the order for such medical procedures may be implemented. Such an authorization process typically requires time spent exclusively on detailing the need for the recommended medical procedure for a particular patient, wherein the authorization process likely involves gathering medical data related to the particular patient, wherein the medical data gathered is specifically relevant to the particular medical procedure for which the order is recommended. Moreover, justification as to why a particular procedure is necessary for a particular patient is likely a prerequisite before an insurance provider will authorize payment for such procedure.

Along with this data-gathering process, there is likely needed data entry of the relevant data in some type of format, whether that occurs on a local network system or on a website or some other platform. Thus, given the inefficiency of current practice relating to a disconnect between a system for injecting orders for medical procedures into a healthcare network system and the process for receiving authorization for implementing such orders, there is clearly a need for a more efficient and effective system and method for accomplishing these tasks.

SUMMARY OF THE INVENTION

The present invention is fundamentally directed to helping the healthcare system manage its costs and to optimizing the use of nuclear imaging for risk assessment purposes and, more particularly, to enabling efficient and effective determinations whether and how nuclear imaging is likely to be appropriate for a particular patient. Related objects are to help healthcare systems reduce costs, increase efficiency and effectiveness, and reduce wasted time and expenses —both in relation to under-utilization and over-utilization of nuclear imaging. Other related objects are to develop solutions that help healthcare systems manage the risks and liabilities related to nuclear imaging decisions, and to enable lower cost insurance programs and regulatory compliance programs.

It is also an object to provide a system and method that enable accountable care, preferably in a way that can minimize statistically unnecessary testing costs and optimize overall healthcare costs, particularly in the contexts of 21st century healthcare reforms in America. In keeping with the concepts of accountability and optimization, the disclosed system and methods include an improved computer-based ordering system for injecting clinical orders into an existing EMR system such that an order for nuclear imaging includes reference to most, if not all, relevant data for determining that nuclear imaging is appropriate for a particular patient. Integrated with this relevant data are justifications for injecting such an order that are at least in accordance with published clinical guidelines and other acceptable clinical standards as required for the ultimate authorization to implement the order for nuclear imaging.

Various aspects of the present invention address as much by providing clinical decision software being integrated with EMR systems and comprehensive rules-based processing deployed real-time at the point of patient care, culminating in presentation of various levels of recommended ordering options in real time for the caregiver while he or she is still on location with the patient. Aspects of the invention allow newly entered data and physician discretion to be processed real-time together with data mined from the data available in the patient's EMR record, all to enable nuclear imaging decisions based on practical translations of accepted standards. Mined data should be understood to include all data relevant to determining the appropriateness of nuclear imaging for a patient, in all forms in which such data is entered and stored in the EMR system. Such data forms may include structured data, as well as unstructured data in the form of free-text data or image data from scanned documents. All relevant data extracted from the EMR system is presented to the physician or caretaker in a readily understandable format through the use of a graphical user interface (GUI) incorporated into the disclosed system.

In an exemplary embodiment, the present invention provides a convenient, accurate way for a healthcare provider to assess the risk of cardiovascular disorders in an individual patient, and therefore to assess whether more costly nuclear imaging is appropriate as part of the risk management regimen for that particular patient. The present invention preferably provides such a method in the form of a middleware system that is readily utilized by doctors, nurses, and other healthcare providers. This middleware system employs a variety of techniques for optimizing nuclear imaging for particular patients while providing an improved computer-based ordering system incorporating all relevant data from the patient's EMR records for determining the appropriateness of nuclear imaging and including, in an order for nuclear imaging, relevant clinical guideline-based information justifying the need for particular nuclear imaging procedures for particular patients in compliance with pre-authorization procedures. Furthermore, with some preferred embodiments, implementation of a recommended order for nuclear imaging may require authorization, wherein the middleware system, in combination with an authorization system, may enable operability of a nuclear imaging device for the purpose of performing a nuclear imaging procedure in relation to a particular patient.

Many other objects, features, advantages, benefits, improvements and non-obvious unique aspects of the present invention, as well as the prior problems, obstacles, limitations and challenges that are addressed, will be evident to the reader who is skilled in the art, particularly when this application is considered in light of the prior art. It is intended that such objects, features, advantages, benefits, improvements and non-obvious unique aspects are within the scope of the present invention, the scope of which is limited only by any claims of this and any related patent applications, and any amendments thereto.

To the accomplishment of all the above, it should be recognized that this invention may be embodied in the form illustrated in the accompanying drawings, attention being called to the fact, however, that the drawings are illustrative only, and that changes may be made in the specifics illustrated or described.

BRIEF DESCRIPTION OF THE DRAWINGS

FIG. 2 is a table showing risk levels and factors for determining a Framingham Risk Score.

DETAILED DESCRIPTION OF PREFERRED EMBODIMENTS

Figure 1:
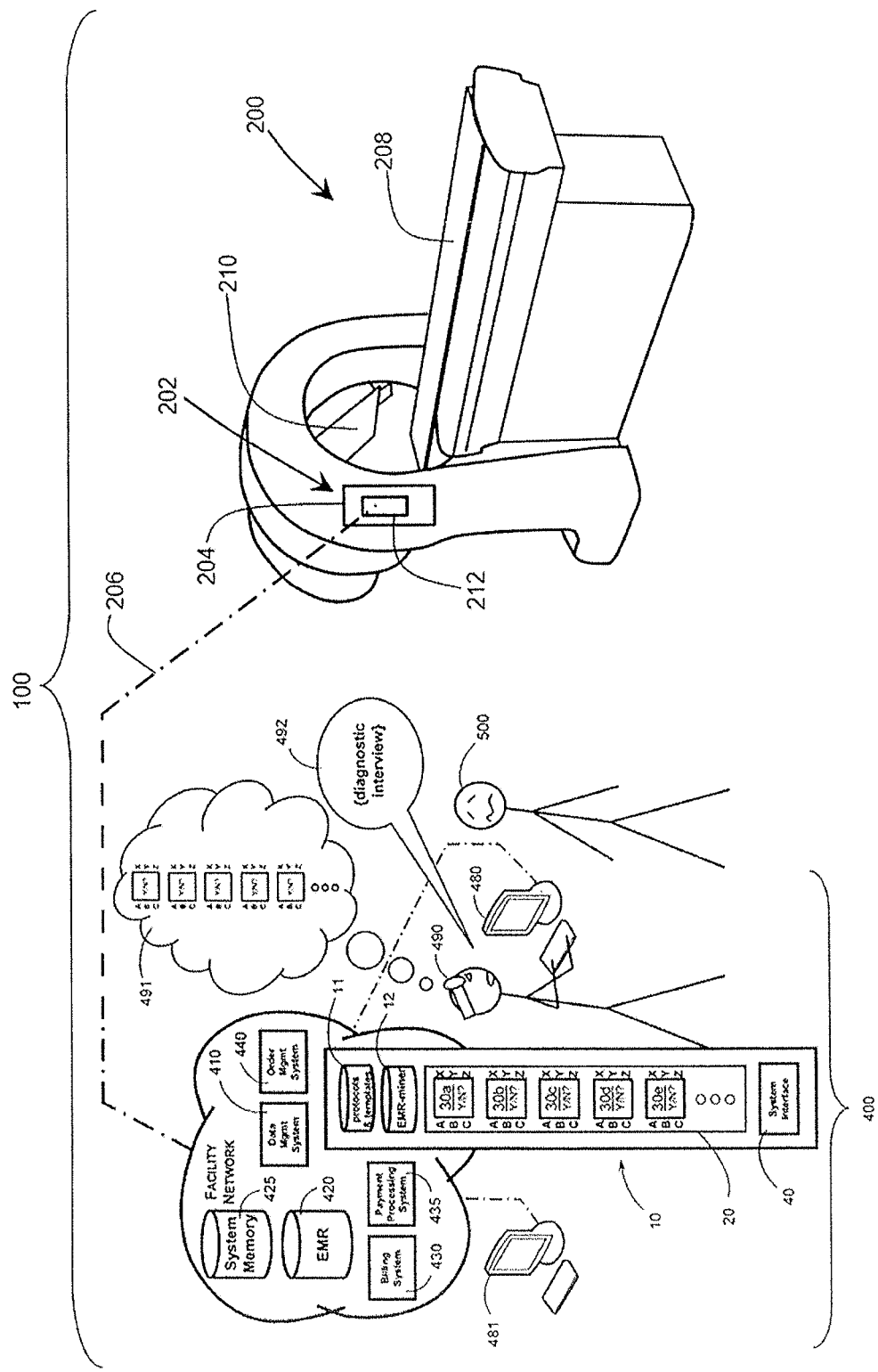
FIG. 1 is a schematic illustration of a typical preferred embodiment of system 10 deployed as a middleware system for supporting care and clinical decisions relative to patient 500.

FIGS. 1-8D are provided to help illustrate and illuminate aspects of preferred and alternative embodiments of the present invention. Although somewhat redundant in various respects, also attached as Appendix A (incorporated here in its entirety by this reference) is a compilation of supplemental information that may help to further illuminate aspects of preferred and alternative embodiments for the benefit of those having ordinary skill in the art.

The present invention provides and enables straightforward methods and systems by which healthcare professionals can determine whether, when and how nuclear imaging is likely to be suitable and appropriate as a risk assessment tool for a particular patient. Preferred embodiments are particularly adapted for use in helping determine a reliable and practical variation of a patient's current FRS and using as much, together with other scores and factors, to guide and support the nuclear imaging and clinical decision process in relation to patients, especially for asymptomatic patients, who may still be at risk of cardiovascular disorders. At the outset, although the descriptions herein focus on nuclear imaging, it should be understood that the system and methods herein described could also function in a similar manner with respect to other types of diseases or disorders and any corresponding relevant medical procedures including, but not limited to, an echocardiogram, a computerized tomography (CT) scan, as well as other medical procedures.

Disclosed embodiments are particularly beneficial for helping healthcare personnel decide whether nuclear imaging is an appropriate risk management procedure for a particular patient, and providing improved utility when injecting an order for a procedure and implementing the order when nuclear imaging is recommended. Embodiments preferably help care providers evaluate a patient's FRS in the context other factors that enable practical and efficient yet reliable nuclear imaging determinations. It should be understood, however, that aspects of various embodiments may be used with scoring systems other than the FRS and for purposes of making other decisions relative to the care and overall management of patients at risk of cardiovascular disorders, such as for determining whether and when to consider risk reduction interventions, and for cost effective management of insurance programs.

For purposes of these descriptions, absent other express or implied limitation, the "FRS" designation should be understood to designate any variation of the Framingham Risk Score, including variations that may arise, in the future, as well as variations that may not be widely accepted but are nonetheless evident from this description or other publicly available descriptions of the FRS and its use.

Also, the phrases "cardiovascular disorder" and "risk of cardiovascular disorder" should be understood in a very broad sense, as any event, disease, injury, disorder or other condition, including without limitation one or more of coronary, cerebral or peripheral vascular disease, stroke, aneurysm or any other potentially serious brain, cardiac and/or cardiovascular episode, and any appreciable risk of any potentially serious cardiovascular disorder, respectively.

With reference to FIG. 1, there is shown a symbolic representation of a typical preferred embodiment of the present invention deployed as Nuclear Care Path system 100 employing a middleware system 10 for supporting nuclear imaging decisions and other clinical decisions by Professional Caregiver 490 relative to patient 500. System 10 and the support it provides are both knowledge-based and flexibly-intelligent. The system 10 is knowledge-based in that guidance and recommendations are provided to Caregiver 490 based on both pre-existing and newly-entered information about patient 500. Pre-existing information is gathered by background processes of system 10 from the data network 400 for the given facility and/or healthcare network, which is preferably a secure network that stores pre-existing information in both Electronic Medical Records (EMR) 420 and other memory systems 425. Although FIG. 1 shows only one EMR system 420, operation of system 10 may include extraction of relevant medical data from more than one EMR system 420, wherein the relevant medical data relates to a particular patient 500 identified by system 10 as described herein.

The support provided by system 10 is also flexibly-intelligent in that it uses an intelligent rules-based approach to both ask and predict answers to various queries while also allowing for the information gathered from the facility network system 400 to be augmented, updated, verified or overridden by information or discretionary override newly-entered by Professional Caregiver 490, to the extent permitted by and consistent with a rules-based engine 20 of system 10.

As depicted by the graphic thought process 491 in FIG. 1, caregiver 490 is generally trained to consider various factors A, B, and C in determining whether, when, and how to perform nuclear imaging procedures relative to patient 500. Although previously gathered information can be helpful, such nuclear imaging determinations are typically ultimately based on the caregiver's personal observation and on the answers to questions explored during interviews 492 with the patient 500 or other persons with pertinent knowledge.

To facilitate and support the caregiver's nuclear imaging decisions 30a-30e that have been chosen and tailored according to the present invention, preferred embodiments of the present invention include software referenced as rules engine 20 that is programmed to provide, generally, for the determination of such decision points 30a-30e. Decision points 30*a*-30*e* may be more or less numerous than five decision points in preferred embodiments, but points 30*a*-30*e* are shown for illustration. In some preferred embodiments, each such decision point 30*a*-30*e*, individually or together with other ones of decision points 30*a*-30*e*, corresponds to whether or not one or more particular procedures are indicated. With each such decision point 30*a*-30*e*, system 10 preferably also makes and/or helps the caregiver decide secondary choices and/or detail steps X, Y, and/or Z. It should be understood that the graphical representation of secondary choices and/or detail steps X, Y, and Z is an exemplary reference to any number of such secondary choices and/or detail steps that are secondary to each of the corresponding procedural decision points 30*a*-30*e*, which should be followed if the particular corresponding procedure is or is not indicated.

In a preferred embodiment, the method and system 10 are provided via computer software, either via the internet, via a stand-alone software application operating independently or in connection with other software systems, or some combination of the two. Some preferred embodiments may be characterized as middleware in that they are adapted to interface with and work in conjunction with an independent data management system 410 and associated electronic medical records systems 420 of the corresponding healthcare facility and/or healthcare network 400. It is contemplated, however, that any other suitable means, even possibly involving completion of a paper form, may also be used in alternative embodiments, all to the extent permitted within a proper construction of the scope of the claimed invention.

As well, embodiments may come in any known form and may also be implemented by hardware, software, scripting languages, firmware, middleware, microcode, hardware description languages, and/or any combination thereof. When implemented with coded programming, it should also be understood that the program code or code segments to perform the necessary steps or tasks of alternative embodiments may be coded in solid state or may be stored in a machine-readable medium such as a computer storage medium. A code segment or machine-executable step or instruction may represent a procedure, a function, a subprogram, a program, a routine, a subroutine, a module, a software package, a script, a class, or any combination of instructions, data structures, and/or program statements. Executable code segments may also be coupled to other code segments or to a hardware circuit by passing and/or receiving information, data, arguments, parameters, and/or memory contents, which may be passed, forwarded, or transmitted via any suitable means including memory sharing, message passing, token passing, network transmission, etc.

With reference again to FIG. 1, a particularly preferred embodiment is provided in the form of a software middleware system 10 that is installed and adapted to interact with the databases, servers, and terminals 480-481 of a data management system 410 of a medical facility or analogous computerized medical network 400. Such system 10 is implemented and adapted to support caregivers by guiding them through a series of questions of factors A, B, and C in order to resolve the particular corresponding decision point 30*a*-30*e*. It should be understood that the graphical representation of questions (or factors) A, B, and C is an exemplary reference to any number of questions and associated algorithmic logic necessary for resolving each respective decision point 30*a*-30*e*, which in turn depend on the particular decision point and the chosen methodology for making that decision according to some embodiments. As depicted by the graphical correlation with the thought process 491, some preferred embodiments of such decision points 30*a*-30*e* are somewhat parallel to the various procedural decisions that caregiver 490 is generally trained to consider in determining whether, when, and how to perform various procedures relative to patient 500, to aid caregiver 490 in making nuclear imaging decisions relative to care of patient 500.

Further, system 10 is implemented and adapted to support caregiver 490 in methodically advancing through decision points 30*a*-30*e*, while simultaneously running background processes to mine for additional relevant data stored in the facility's EMR system 420. While the caregiver 490 is guided through questions A, B, and C corresponding to each decision point, system 10 uses the additional relevant data mined from the EMR system 420 to propose and/or provide predicted answers to some or all of the same questions A, B, and C. Once each question for a particular decision point 30 is completed or otherwise satisfied, generally either by a new entry by the caregiver 490 or by the caregiver's acceptance or validation of the default answers or the answers derived from the EMR system 420, system 10 then presents final recommended options for ordering nuclear imaging or training or interventions, or for conducting further tests or seeking further consult, for the corresponding decision point 30. At various opportunities throughout the overall process, system 10 allows caregiver 490 to supplement, validate, and/or predict final entries for each applicable question A, B, and C, as well each secondary consideration X, Y, and Z.

Shown in FIG. 1 is a general representation of a nuclear imaging device for administering cardiac nuclear imaging to a particular patient 500 subsequent to injecting an authorized order generated by system 10 into EMR system 420 for nuclear imaging. Although FIG. 1 illustrates a particular device, any device capable for use in administering cardiac nuclear imaging is contemplated for use with the disclosed system and method. An acceptable nuclear imaging device will likely provide a surface 208 onto which patient 500 can be positioned during operation of the nuclear imaging device 200. In some preferred embodiments, surface 208 is a horizontal table-like structure. Surface 208 may also be configured to be adjustable such that the position of the patient may be modified during implementation of a nuclear imaging procedure. In other embodiments, instead of a horizontal surface, some nuclear imaging devices may incorporate a chair (not shown) in which patient 500 sits in a generally more upright position during operation of the nuclear imaging device 200.

Also incorporated in the nuclear imaging device are one or more image capture devices such as gamma cameras 210. The gamma camera 210 may be fixed in position at a particular angle on the nuclear imaging device, with the position being best-suited for capturing images of a particular portion or region of the body of patient 500. Other nuclear imaging devices may incorporate gamma cameras which are moveable, for instance in a rotatable motion, around patient 500, while capturing images of patient 500 during operation of the nuclear imaging device 200, such as those devices which perform single-photon emission computed tomography (SPECT).

A typical nuclear imaging scan consists of several components. Nuclear material (commonly referred to as a radiotracer) that emits gamma rays is injected into a patient 500. When using a nuclear imaging device 200 such as that illustrated in FIG. 1, the patient 500 would lie on a flat horizontal surface or table 208. As previously indicated, other nuclear imaging devices may incorporate a chair-type device (not shown) wherein the patient 500 is scanned in more of a seated position instead of lying prone on a table 208. In some embodiments, including when the nuclear imaging procedure is a SPECT scan, the table 208 may be moveable in order to appropriately position the patient 500 for capturing images with the gamma camera 210. The gamma camera 210 is able to capture functional images of the patient's internal biological structures (e.g., the heart and/or associated portions of the circulatory system) for the purpose of evaluating the present condition of the patient 500.

Integrated with system 10, in conjunction with nuclear imaging device 200, is an associated authorization system 202 which includes a mechanism for preventing the operation of the nuclear imaging device without authorization. In some embodiments, the mechanism may be represented by device lockout 204. Device lockout 204 may include an electronic mechanism incorporating a disconnect panel 212 in network communication with system 10, wherein disconnect panel 212 may include a circuit breaker or other similar device which is in-line with the typical power supply system for providing power to operate nuclear imaging device 200. Disconnect panel 212 can be used to interrupt the flow of electricity for operating nuclear imaging device 200 such that nuclear imaging device 200 is not operable without prior authorization. It will be understood that disconnect panel 212 may be incorporated and integrated with nuclear imaging device 200 in some embodiments while disconnect panel 212 may also be a separate component in other embodiments.

A default mode may be that nuclear imaging device 200 is not operable due to lockout device 204 interrupting the flow of electricity for powering nuclear imaging device 200. Upon authorization of a procedure in which nuclear imaging device 200 is intended to be used as a diagnostic tool with respect to a particular patient, system 10 is operable to communicate a signal via secure network connection 206 which disables device lockout 204, restoring the flow of electricity to nuclear imaging device 200 such that nuclear imaging device 200 is usable for its intended purpose. Network connection 206 may be a wired or wireless connection.

In other embodiments, device lockout 204 may be a mechanical mechanism for preventing operation of nuclear imaging device 200 without prior authorization. In such other embodiments, disabling of device lockout 204 so that nuclear imaging device 200 is only operable for performing an authorized imaging procedure on a particular patient may be implemented by a designated device operator.

When an order for a nuclear imaging procedure for a particular patient 500 is injected into EMR system 420 by system 10, an authorization indication will allow operation of nuclear imaging device 200 for implementing nuclear imaging for a particular patient 500. In some embodiments, system 10 is connected to authorization system via a secured network connection 206 such that authorization to perform a nuclear imaging procedure utilizing nuclear imaging device 200 is sent by system 10 via secured network connection 206 to nuclear imaging device 200. Once authorization is received, device lockout 204 essentially unlocks nuclear imaging device 200 such that nuclear imaging device 200 is operable to perform the nuclear imaging scan as ordered. The secured network connection 206 can be either a wired configuration or a wireless configuration. For those embodiments in which device lockout 204 employs a mechanical mechanism for preventing operation of nuclear imaging device 200 without prior authorization, a designated device operator may physically unlock nuclear imaging device 200 prior to performing an authorized nuclear imaging procedure.

When system 10 recommends a nuclear imaging procedure for a particular patient 500, and the recommendation is accepted such that an order is injected into EMR system 420, system 10 generates the order such that it contains all relevant data extracted from EMR system 420 which is used by system 10 to generate the recommendation. Furthermore, and based on the relevant data used for making the determination that nuclear imaging is appropriate for a particular patient 500, system 10 provides justification for the order on the face of the order which justifies the necessity for the nuclear imaging procedure. Justifications included on the order are based in part on and in compliance with published clinical guidelines and the determinations made by system 10 as illustrated in the flowcharts illustrated in FIGS. 3 and 4.

Preferably, to provide evidence-based caregiver support for clinical decisions, system 10 is further adapted to provide the same access to clinical information, support, and resulting recommendations and to facilitate and enable final order execution relative to a particular patient 500 through multiple convenient terminals 480, 481, which are conveniently located in close proximity to multiple possible points of care for patient 500. System 10 preferably uses the existing information systems of facility 400 to interface with the facility EMR system 420 and data management system 410. The integration with network 400, more particularly integration with one or more EMR systems 420, preferably allows system 10 to safely locate, interpret, and extract patient data from electronic medical records 420, reformat the patient data through normalization of the extracted patient data into a form usable by system 10, and to create readily-executable ordering options for caregiver 490 to consider, revise, reject, or approve relative to nuclear imaging or otherwise in the management of the patient's cardiovascular conditions.

One particular aspect relating to the operation of system 10 involves the interaction of physician 490 with system 10 through a graphic user interface (GUI) 300. System 10 provides condition-specific data extracted from one or more EMR systems 420 for purposes of creating orders for procedures, more particularly nuclear imaging procedure orders.

Data extracted from EMR 420 may be of several types, including structured data or unstructured data. Unstructured data may be in the form of free text or scanned documents and images. Moreover, data may be retrieved from more than one source, including multiple EMR systems 420. For example, structured data may include laboratory test results and the like. Free-text data could include written chart notations entered by a physician or technician 490 during patient encounters. Images could represent any type of data in a document which is scanned into EMR system 420 for inclusion into the records of a particular patient 500.

In order for system 10 to utilize all forms of data which might be relevant with respect to which care path, if any, is recommended for a particular patient 500, the data must be converted into a format which can be used by system 10 through the process of semantic normalization. For instance, during the normalization process, domain-specific terms are assigned to structured data for use with system 10.

For structured data stored in EMR 420, there is likely a medical code assigned to the data in accordance with specific medical coding protocols, such as Current Procedural Technology (CPT), Logical Observation Identifiers Names and Codes (LOINC), International Classification of Diseases (ICD), Systemized Nomenclature of Medicine-Clinical Terms (SNOWMED-CT), RxNorm, and the like. As would be understood by those of ordinary skill in the art, the medical code assigned to particular data is dependent on the type of data that is represented. Structured data is readily accessible by system 10 from EMR system 420.

For other types of data that are not stored as structured data in EMR system 420 such as free text or scanned documents, a medical code may also be assigned after the substance of such data is extracted by system 10. For example, in order for system 10 to extract unstructured data in the form of free text from EMR 420, system 10 employs natural language processing (NLP) to extract and render the data into a format that is readily usable within system 10. Candidate sentences are extracted from the text using certain keywords. Once a candidate sentence is extracted from the text of data stored in EMR system 10, the candidate sentence is then sent to and processed by a NLP engine using techniques such as tokenization, part-of-speech marking, named entity recognition, and the like. With scanned documents or images, system 10 extracts the data from the scanned document or image by employing optical character recognition (OCR) techniques on the document or image to convert the image data to free-text data. Then, in accordance with the process described above, the information contained in the newly created free-text data is extracted by system 10 through the use of natural language processing.

After completing this process and natural language processing is used in order to convert the free-text data to structured data, this structured data may then be normalized for use in system 10, as described in more detail below. As described above, with respect to scanned documents or images, the first step is for system 10 to perform OCR in order to extract the data in the scanned or image format and to convert this data type into free text. During OCR, the scanned document or image is pre-processed in order to enhance readability. Once this OCR step is completed, the resulting free-text data can be converted to structured data as previously described using natural language processing.

In the process of extracting usable relevant data from EMR system 420, such data is normalized by system 10. Data extracted from EMR system 420 by system 10 is necessarily in the default format assigned by EMR system 420. Examples of default EMR formats include JavaScript Object Notation (JSON) and Extensible Markup Language (XML). The JSON or XML data is generally structured as a tree structure such as a key to value data structure. A two-step data normalization process is employed by system 10 in order to convert the data extracted from EMR system 420 to a format which is usable and understandable in the context of system 10.

The first step in normalizing the extracted data involves structural normalization. More particularly, structural normalization involves understanding which field or key contains which data. So that system 10 can utilize the data extracted from EMR system 420, the data is configured into a data structure which allows system 10 to store the data values extracted from EMR system 420. Some extracted data values will be modified by system 10 in the structural normalization step. For instance, an order placed by physician 490 may have a status of "PENDING" in one particular EMR system 420. In another EMR system 420, such a pending order may have a status of "NOT DONE." When this data is extracted by system 10 from each of the EMR systems 420, each status will be converted to "PENDING" in the format which system 10 stores such data values.

Continuing with the normalization of the data extracted from EMR system 420 by system 10, the second step involved is semantic normalization. In the semantic normalization step, meaning is derived from the data extracted by system 10 based on data type. For instance, when a data value extracted from EMR system 420 is a test result, the meaning of such test result is deciphered by system 10 during semantic normalization in order for the test result to play a meaningful role in determining the appropriateness of instituting a further care path for a particular patient 500. As an example, if the test result indicates levels of low-density lipoprotein (LDL) for a particular patient 500, this test result might be referenced in EMR system 420 as "LDL calc," "LDL in serum," or other similar data values. In order to be effective when determining the appropriateness of a further care path, system 10 must recognize that each of these designations refers to the same test result. To that end, system 10 assigns medical codes to all data extracted from EMR system 420. These medical codes may be from any known medical coding system including, but not limited to, ICD-9/ICD-10, LOINC, SNOMED-CT, CPT, RxNorm, and others.

With particular application to the NUC care path module, another layer is involved which understands what the decision support inputs are in relation to the data extracted from EMR system 420 by system 10. As a non-limiting example, if a particular patient has been previously diagnosed with hypertension, such diagnosis will appear in that patient's records stored in EMR system 420, wherein the diagnosis might appear as "HasHypertension" in the patient's electronic medical records. This indication of "HasHypertension" appearing in the patient's electronic medical records is referred to as a data point which contains either True or False. The data point is configured to look for certain medical codes and statuses. In this particular example, "HasHypertension" searches through the normalized data for problems or conditions with SNOWMED codes related to the particular condition. In addition, the "HasHypertension" data point ensures that the problem or condition is designated as "Active."

Such data points are then fed into a binary decision tree whose leaves are either a recommendation to act or to do nothing. The recommendation may include a recommendation that a particular procedure such as nuclear imaging, echocardiogram, or the like, be performed on the particular patient. Importantly, when a particular care path is recommended for a particular patient, the leaves not only contain a recommendation but also an explanation for why a particular procedure is recommended, using an amalgam of the patient's data and clinical guidelines. For instance, a recommendation for a particular patient might read as follows: "Patient is >65 years old (75 years), had a recent PCI (Percutaneous Coronary Intervention) on May 1, 2014 without an echocardiogram follow-up and is thus eligible for stress testing." As can be readily understood by the format of this particular example recommendation, this is not only a recommendation created by system 10 for a particular care path directed for a particular patient 500, but system 10 also incorporates into the recommendation the relevant patient data extracted from EMR system 420 by system 10 as well as a justification for the recommendation applying clinical guideline-based rules as to why system 10 recommends the particular care path for the particular patient 500.

Having the ability to utilize all types of data stored in EMR system 420 is important for a determination of the proper care path for a particular patient 500 utilizing system 10. For example, when a particular patient 500 undergoes an echocardiogram (ECG), the technician or physician 490 may record a value of the measurement of left ventricular ejection fraction in the patient's records which is entered as free text. In order to gain a more complete understanding of the condition of a particular patient 500, a physician 490 would likely want to observe the progression of the LVEF measurements for the patient 500 over time. As part of providing a complete snapshot of the patient 500 for proper evaluation by physician 490 in the present example, system 10 would extract all of the data related to LVEF measurements from any such free-text documents, and using natural language processing, this data can then be converted to discrete data elements usable by system 10 through normalization of the data. Once normalized, system 10 can then display the LVEF data over time in a graphical format on GUI 300 which readily indicates the progression of the patient's condition over time for a more efficient and effective evaluation of the particular patient's condition by physician 490.

A general method according to preferred embodiments includes, generally, determining whether a particular patient 500 meets criteria for whether nuclear imaging is suitable and appropriate, providing an option for the caregiver to order as much if appropriate criteria are met (or, alternatively, if exclusion criteria are not met), and evaluating and making further ordering options available depending on whether or not nuclear imaging is likely to be appropriate based on calculated values for FRS and other scores and factors, some of which closely follow published clinical guidelines.

The method preferably includes extracting all relevant data from one or more EMR systems 420 stored in a patient's records, as described above, in order to determine whether that patient 500 meets the criteria for appropriateness of having nuclear imaging performed or, alternatively, whether the patient 500 meets the criteria for NOT having such imaging performed. Once the health care provider 490 has entered and/or approved sufficient data entries for the system to complete a recommended order option, the data processing system then analyzes the data and corresponding selections and advises the health care provider 490 as to whether or not nuclear imaging is appropriate, or whether it is discretionary.

In between inappropriate and appropriate, preferred methods also present options whenever the appropriateness would be considered discretionary to the healthcare professional and/or an oversight review board or the like. Preferably, the health care provider 490 and/or board in discretionary cases are provided with a list of the factors weighing for and against appropriateness and, the decision maker is automatically prompted to enter his or her rationale for exercising such discretion one way or the other.

If the rules engine projects that nuclear imaging is suitable and appropriate, that is, if the patient 500 meets the rules engine criteria, the health care provider 490 is presented with the option to execute an order for a nuclear imaging procedure for that patient 500. Once the caregiver approves the corresponding ordering option for a particular patient 500, the system initiates an ordering procedure which automatically drives scheduling and billing processes. In either clear case, if it is determined that nuclear imaging procedure is appropriate or, alternatively, not appropriate, then the analysis proceeds as illustrated in the FIGS. 3 and 4.

Although various scores and factors may be implemented in accord with the present invention, FIG. 2 provides an outline of the factors and resulting scoring for determining the FRS of the preferred embodiment, which is slightly different for a male or female patient 500 in accordance with the teachings of the present method. During analysis of data for determining FRS and consequential decisions, a variety of factors are assessed. More particularly, there are three levels of Nuclear Appropriateness determined by the more preferred embodiments. For asymptomatic patients 500, the actions can be Appropriate (7-9), Uncertain (4-6), and Potentially Inappropriate (1-3). The system is preferably programmed to present an option to order nuclear imaging tests for the patient 500 for both Appropriate and Uncertain levels, according to an Order Approval template (FIG. 8). Whereas, if a patient 500 is deemed Potentially Inappropriate by the NUC module care path, there will be no Accept or Decline buttons presented in the NUC section on the Order Approval template.

Figure 3:
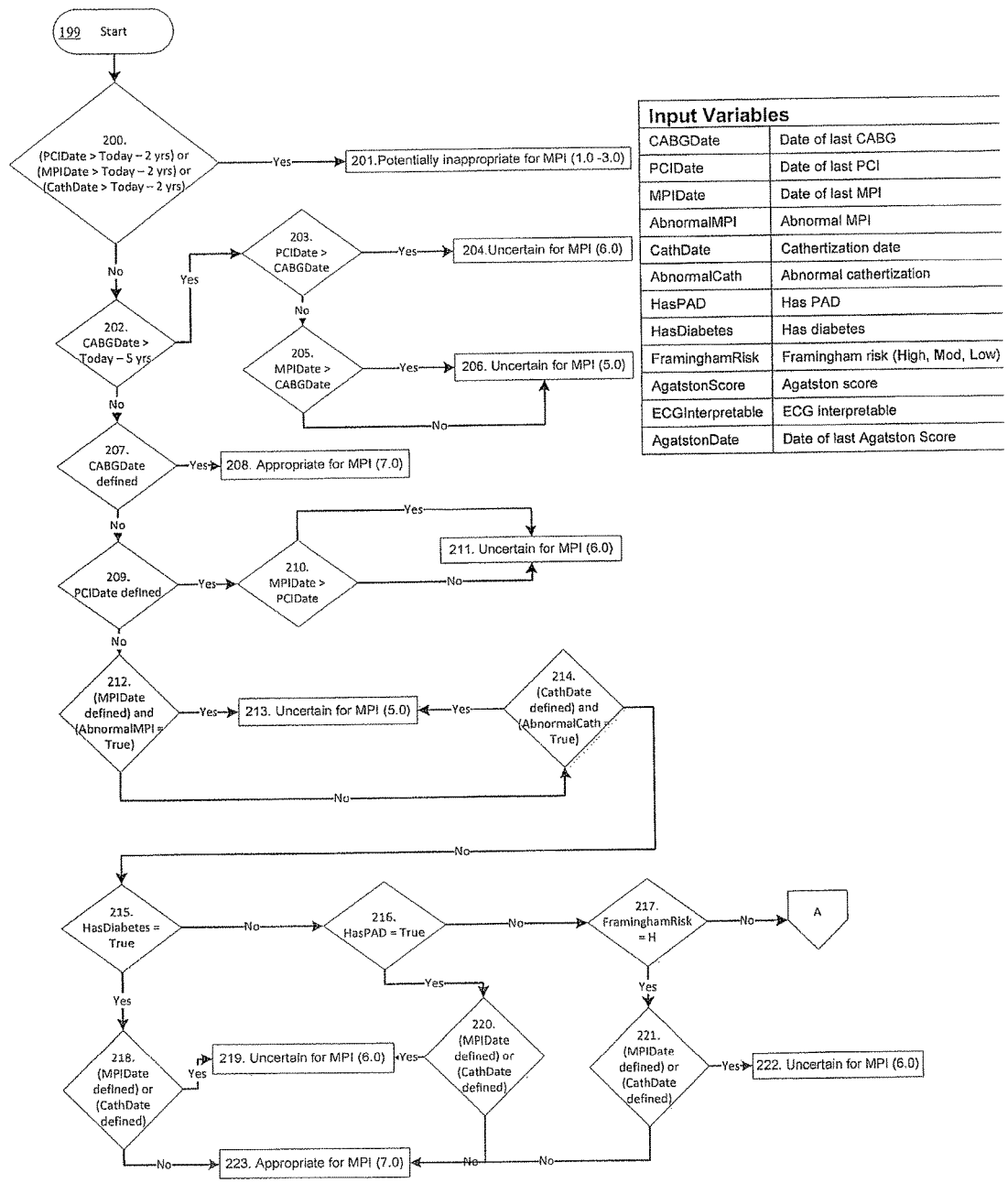
FIG. 3 is a schematic flow diagram of method steps of an embodiment associated with cardiac disorder diagnosis, prevention, and protocols for evaluating appropriateness of nuclear imaging.

Although not discretely shown in the flowchart of FIG. 3, the start box 199 also entails an initial factor of assessing whether the patient 500 is symptomatic of cardiovascular disorder. If the patient 500 is symptomatic, then the rules engine 20 will automatically shortcut the rest of the rules-based assessment by immediately prompting the option to order nuclear imaging. As will be evident, such initial factor may be practically achieved at other procedural levels simply by not initiating the nuclear imaging care path unless the patient 500 is asymptomatic.

Returning now to FIG. 3, the schematic provided shows additional steps of an order approval protocol developed in accordance with the teachings of the present method. The method proceeds along one of two major paths, depending upon whether a given patient 500 has been initially selected for inclusion or exclusion in the SCA protocol.

System 10 automatically extracts all relevant data (including age, gender, smoking history, systolic blood pressure, hypertension medications, HDL and Total Cholesterol) from EMR system 420 which is necessary for determining a Framingham Risk Score and calculates a Framingham Risk Score for the patient 500. The relevant data may be in the form of structured data or unstructured data. If unstructured data, system 10 operates to convert such data to structured data utilizing natural language processing and/or optical character recognition depending on if the unstructured data is free text or images. If a piece of the required data is not found in the patient's chart, a message will be displayed at the bottom of the Symptoms template to indicate what is missing, such as by presenting the message, "NO DATA for: HDL." Such a message is visible at the bottom of the symptoms pop-up window shown in FIG. 7.

Since age and gender are required patient data and vital signs are required to be filled out before the Symptoms template is opened, the most common piece of data to be missing is lipid information for HDL and Total Cholesterol. If the data is not available, the care path will not process and the provider 490 will see a message "Value is required" and "Framingham Risk" on the Order approval template. The Framingham Risk field will display what data is missing for the calculation.

The NUC (Nuclear Appropriateness) care path module may also require input by the provider 490 to finish processing. Possible data entry questions for the NUC care path include if the patient's most recent MPI or Cath was abnormal, and if the patient's ECG is interpretable. The data entry pop ups for Abnormal MPI or Cath provide a link for easy reference to the patient's MPI or Cath history so the provider 490 can answer the question without needing to leave the SureCare Approval template.

As soon as the provider 490 clicks the answer to the question, the NUC care path will reprocess using the new data. If further data entry is required, the pop up will display again with the new question. If there is no further data entry, the care path will complete processing and display any recommended actions.

Some preferred embodiments provide much of such functionality through a middleware system 10 such as graphically illustrated in FIG. 1, which is adapted to interface with the data management systems 410 to guide physician caregiver 490 through a care decision process involving decision points 30*a*-30*e* and related logic that are characteristic of rules engine 20. Through interaction with the network 400 of a healthcare facility or analogous healthcare network, system 10 prompts and causes guidance screen displays to be provided to caregiver 490 on any of the available secure terminals 480-481 of facility network 400, while simultaneously mining additional pertinent data from the corresponding EMR database 420 through interaction with the related management and processing systems 410, 430, 435, and 440.

System 10 preferably operates, and physician caregiver 490 accesses as much, through a graphic user interface home screen (or "HomePage") 300 and related secondary screens, pop-ups and the like that are merged with other interactive data presentations characterized by the network's data management system 410 and its associated EMR system 420.

As represented in the screen shots of FIGS. 5-8, a particularly preferred implementation of the present invention is adapted through software technicians to interface with a popular knowledge-based data management system 410 and/or an associated EMR system 420 such as one commercialized under the "NextGen" product designation. Accordingly, a preferred embodiment of a HomePage 300 for system 10, as shown in the attached FIG. 5, includes various fields, windows, toolbars and the like (collectively "regions") that are dictated entirely by the data management system 410 and that retain the same appearance as is familiar to users of such system 410, such as is the case with EMR menu bar 411 which is the uppermost section of HomePage 300. In contrast, other regions of HomePage 300 are given an appearance and corresponding functionality that is dictated by System 10 and its rules engine 20, such as is the case with a preferred rules engine index bar 310 that is displayed immediately under menu bar 411. Although automated integration is feasible in alternative embodiments, the integration of middleware system 10 with EMR system 420 and other components of network 400 is preferably performed by specialized software technicians during an initial integration and discovery process that adapts system 10 such that its various fields, look-ups, and parameters are mapped to integrate with the particular data structure and discrete data points of facility network 400. During such initial integration and discovery process, additional unique data accommodations are also created to the extent that required data points are missing from system 400 but are otherwise called for by the logic of system 10.

When middleware system 10 is integrated with EMR system 420 and related systems of network 400, system 10 is then ready for use by caregivers 490—also referred to interchangeably as physicians, providers, and/or patient care technicians (PCT) 490. As a result of the integration of system 10 with EMR system 420, system 10 can be launched from directly within the interface of EMR system 420. For example, after successful integration of system 10 with EMR system 420, a clickable icon will appear with the display of EMR system 420 which, when selected by PCT 490, will begin operation of system 10. In operation, system 10 then fully supports caregiver 490 through the process of conducting interviews 492 and making related observations in order to determine what procedures are indicated and/or should be recommended for patient 500, as well as how, when, and other details relating to performing the procedures. Such diagnostic process is guided through use of HomePage 300 by PCT 490, while background processes of system 10 are mining the EMR 420 for all of the pertinent data relating to the particular patient 500 and the particular condition which is being evaluated. For example, when determining whether nuclear imaging is appropriate at a given time for a particular patient 500, system 10 will extract only data from EMR 420 which are relevant for system 10 to evaluate such appropriateness. Moreover, system 10 will extract all of such data that is stored within EMR system 420 which are relevant to determining the appropriateness of nuclear imaging for a particular patient 500, whether that data be structured, free text, or in an image format.

To use system 10 in such preferred embodiments, provider 490 uses one of the available terminals 480, 481 that are networked with facility network 400, preferably during each substantive encounter with patient 500. To commence such a use, PCT 490 clicks appropriate icons and the like to either create a new HomePage 300 that corresponds to patient 500, or opens a pre-existing one if it already exists on network 400. Alternative embodiments automatically locate and/or create such HomePage 300 based on intelligent machine recognition of the presence of patient 500 or a personal identifier accompanying patient 500 (such as a hospital wristband or a unique RFID tag assigned to patient 500).

In the process, PCT 490 is preferably prompted to first designate the type of patient encounter (i.e., "Office Visit") being conducted, by entering appropriate data in region 330 of HomePage 300. In the process, for a routine follow-up visit, preferred embodiments offer the streamlined options for the PCT 490 to just designate a focused type of follow-up patient encounter in order to streamline and simplify the level of prompting provided by system 10, and to watch for and make recommended procedure responses, to be in line with typical abbreviated follow-up visits with a patient 500 who has suffered or is thought to be at risk of suffering from a more particular type of cardiovascular episode.

Either through prompts or natural progression, PCT 490 then begins gathering vital signs for patient 500 and is guided through that process by clicking the "Vital Signs" button 321 of HomePage 300, which then causes a pop-up window to prompt and guide PCT 490 through the process of gathering such vital signs as are required for rules engine 20 to make its recommendations. Until sufficient vital signs have been gathered and/or entered in such Vital Signs pop-up window, the "Vital Signs" button 321 is displayed in a manner to indicate that additional action is required under that pop-up window, such as by displaying the button 321 in the color red or with another alert condition.

Whenever the Patient's HomePage 300 is created or accessed by system 10 and/or PCT 490, the rules engine 20 of the middleware system 10 is preferably adapted to automatically process the data populated and/or entered in the various fields on HomePage 300, in order to intelligently guide and support PCT 490 through both processes and related ordering processes, to determine and propose recommended ordering details and to cause the ordered procedures to be executed when validated (i.e., approved) by PCT 490. Throughout operation of system 10 during each patient encounter, system 10 is also adapted to create and retain (or to cause other processes to create and retain) hidden history files and/or hidden audit trails to enable caregiver 490 or network management or other interested parties to later conduct retrospective and/or systemic evaluations of the care of patient 500 and/or the quality of care being provided through PCT 490 or any particular grouping of caregivers, such as through the entire facility network 400.

Figure 4:
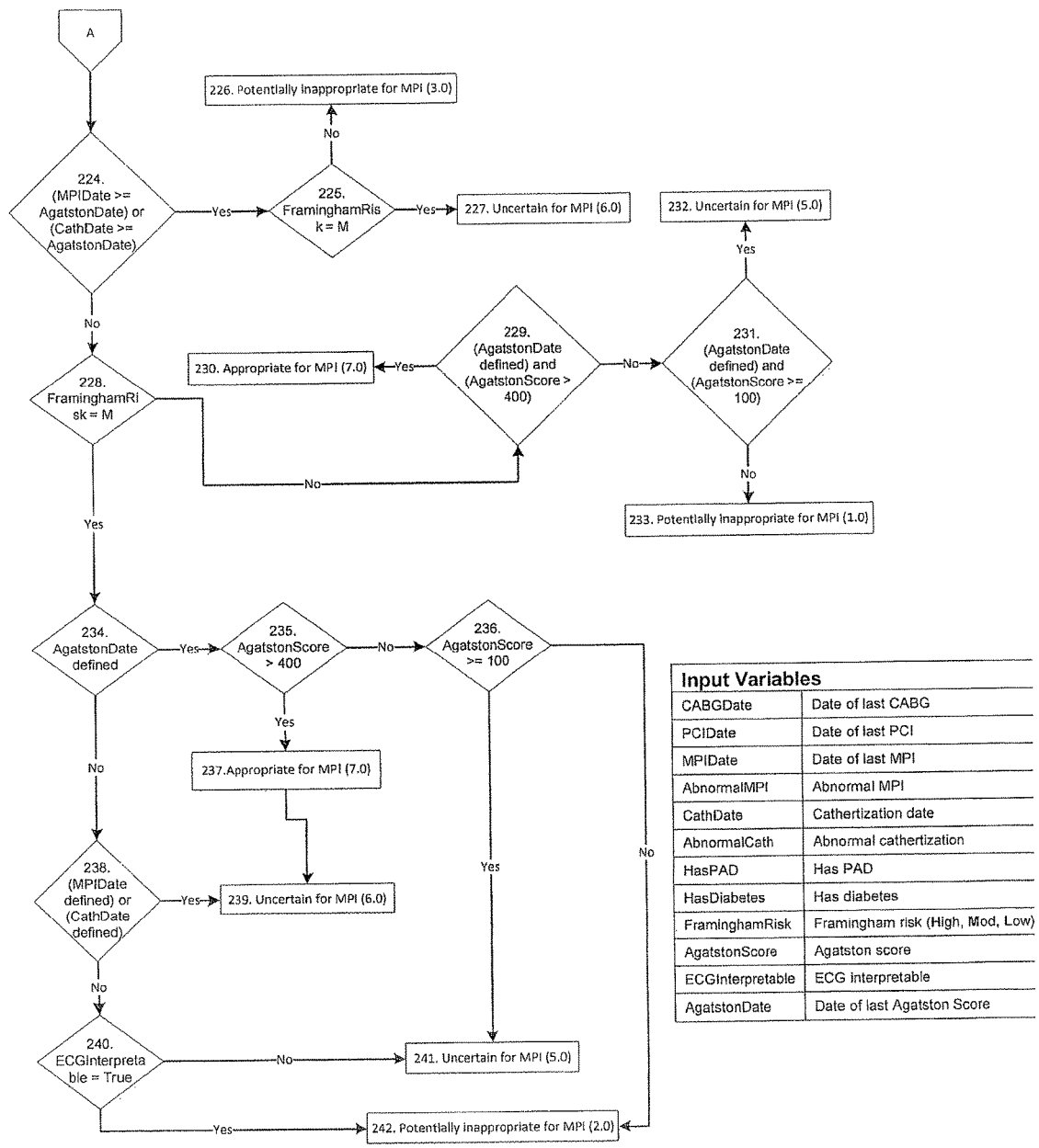
FIG. 4 is a schematic flow diagram of method steps continuing from the flow diagram illustrated in FIG. 3.
Figure 5:
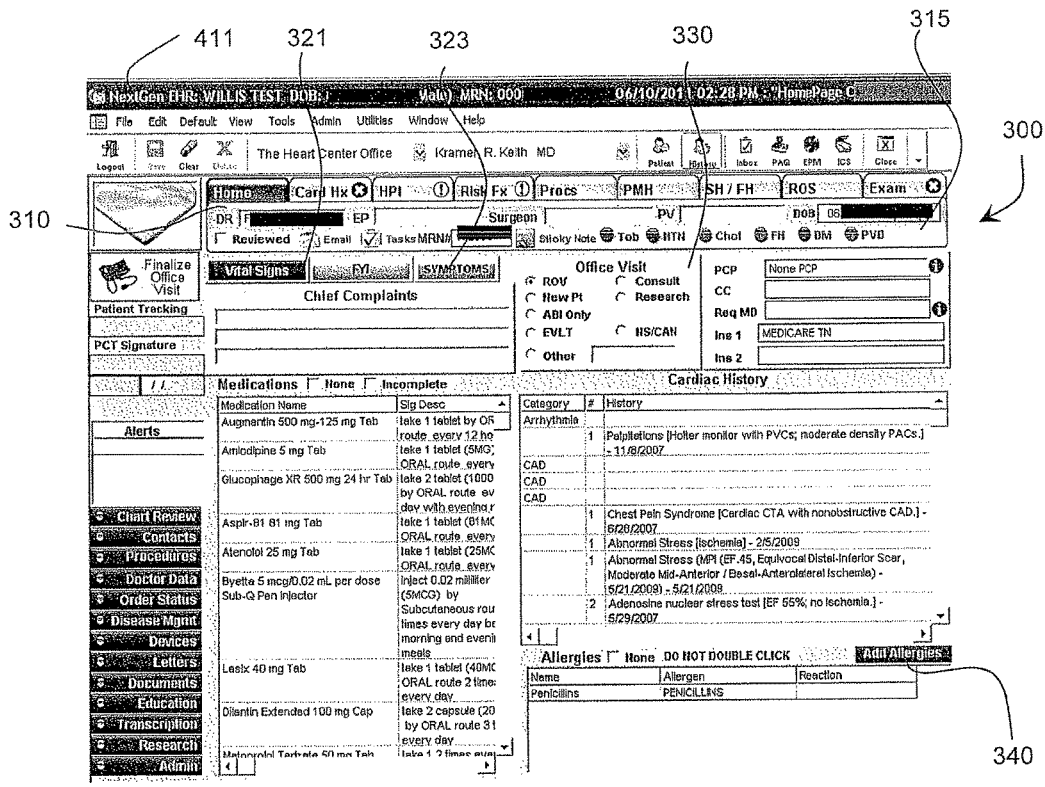
FIG. 5 is a screenshot illustrating a home screen 300 for various aspects of alternative embodiments developed according to the teachings of the disclosed system (portions of which are redacted in this description solely in order to minimize unintended disclosure of possible patient identifiers).
Figures 6, 7:
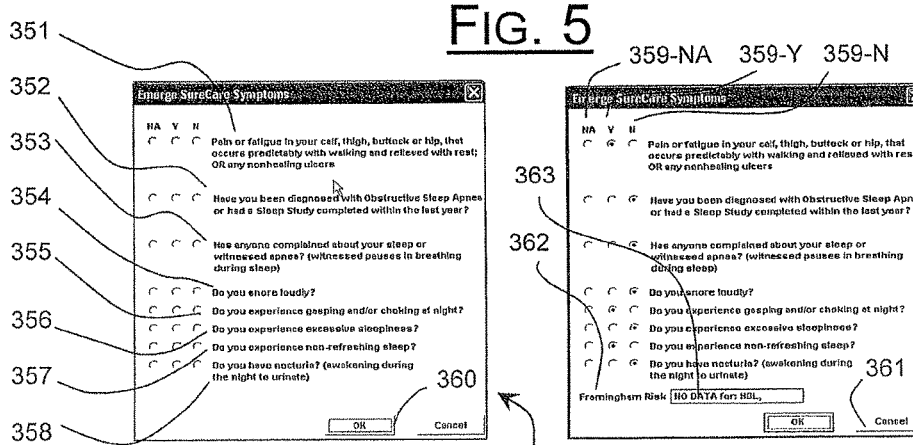
FIGS. 6 & 7 are screenshots illustrating a symptoms pop-up window at two different stages of completion pursuant a preferred embodiment method.
Figures 8A, 8B, 8C, 8D:
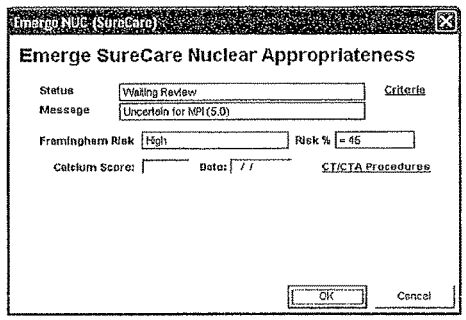
FIG. 8A is a screenshot illustrating a pop-up window indicating status of a recommendation.
FIGS. 8B-8D are screenshots illustrating an order confirmation reporting window 370 of an embodiment developed according to the teachings herein.

More particularly, specific steps of a preferred embodiment (the "NUC module") are illustrated in the flowcharts of FIGS. 3 and 4, with reference to the screen shots shown in FIGS. 5-8, which present the decision tree structure for determining appropriateness of nuclear imaging as a further risk assessment.

Further alternative embodiments include additional patient test results, the preparation of the patient 500 for a better appropriateness decision, and/or the possible option to proceed with ordering appropriate consult to determine whether Radio Frequency Ablation (RFA) or other intervention should be implemented if the risk levels are too high for administrative guidelines for the patient population.

One particularly preferred alternative embodiment capitalizes on the SureCare software product (referred to as the "SureCare System" for purposes of this description), which is commercially available in the United States as of the filing date of this description. Such an embodiment may also use the SureCare software product to enable refined and alternative methodologies and systems that improve the information gathering aspect of preferred embodiments, as well as various patient preparation, counseling and other aspects of preferred embodiments.

The preferred NUC module embodiment is schematically described as beginning at Step 199 as shown in FIG. 3. It should be understood, however, that preferred embodiments further include installation and set-up of such procedural module in a manner that functionally interfaces with a facility's preferred process control systems (for reference, the "Pre-Existing Data Management System") and, preferably, its EMR system 420. Such installation and set-up preferably are performed by expert technicians in a series of meetings and discussions with facility management in order to discover the detail needs of the Pre-Existing Data Management System and to generally achieve a smooth integration with such pre-existing systems. Particular preferred embodiments are tailored for easy interface with popular data management EMR systems 420 such as that commercialized under the "NextGen" designation, which uses a "knowledge-based model" with standardized data mapping to discrete data points, while customization may be needed to add any data points that are missing from the Pre-Existing Data Management System. Hidden data templates, audit trails, and other expedients may be provided to enable such initial set-up as will be evident to those of skill in the art.

Once the overall system has been integrated with other systems as desired, the process for a given patient 500 then begins at Step 199, which may correspond to a home screen. Upon initiation of the home screen process at Step 199, particular designators are selected or entered to identify the patient 500 and whether the patient 500 is a new patient or a prior patient. The identification process may be done through keyboard entry or through barcode wanding or the like, preferably whatever identification technique is customary for the existing EMR System.

Then, assuming the patient 500 is already a patient in the EMR System 42, once the patient 500 is identified with sufficient specificity, background data queries automatically begin gathering and periodically updating discrete data points of relevant information from the Pre-Existing Data Management System. Patient data is extracted from the existing EMR system 420 based on data mapping done by technicians in a pre-installation process. As data is gathered, discrete data elements are accessed, formatted, and verified by an automated process and stored in a specific data collection linked to each encounter. Any persistent flags (like exclusions) are stored in a data collection outside of encounter specific data. Any calculated data points, such as the patient's FRS, are processed by the automated data gathering process once adequate information is available. Throughout preferred use, the data table is then repeatedly and/or continuously being updated by background processes to ensure new data is not entered in the EMR system 420.

Preferred embodiments of system 10 extract only the data which are relevant to the condition being evaluated with regard to a particular patient 500. For example, when determining the appropriate care path with respect to a nuclear imaging protocol, only data related to cardiovascular disorders which are or could be considered relevant to the determination of the appropriateness of nuclear imaging is extracted from EMR system 420. Such data are related to the determinations made by system 10 as illustrated in the flowcharts shown in FIGS. 3 and 4. These determinations, using discrete data elements extracted from EMR system 420 by system 10, are based in part on relevant published clinical guidelines with respect to prior test results, procedures, and evaluated conditions, and on particular modifications to those guidelines as directed and indicated in the data used by system 10 for making the determinations reflected in the flowcharts of FIGS. 3 and 4. In other words, any determinations made by system 10 with respect to whether nuclear imaging is appropriate for a particular patient 500 are based on a combination of both published clinical guidelines standards as well as more particular standards which are related to but not specifically addressed in the clinical guidelines. For example, whereas the published clinical guidelines take into account the date of the most recent of certain cardiac procedures on an individual basis, system 10 not only considers this data but also compares the dates of each cardiac procedure discussed in the published clinical guidelines for making a determination with respect to the appropriateness of nuclear imaging for a particular patient 500. Moreover, in some instances, system 10 considers date data regarding additional cardiac procedures which the published guidelines do not address. Thus, the determination of whether nuclear imaging is appropriate for a particular patient 500 as recommended by system 10 is based on more data which results in a more thorough evaluation of the condition of and risk to a particular patient 500.

Preferred embodiments of the NUC care path may also prompt the care provider 490 for additional input for data that relies on the provider's assessment of the patient's specific condition (normal/abnormal test results, optimal medical therapy levels) that the automated data gathering is not able to determine reliably. Preferably, these prompts only occur if the care path requires the data to continue processing.

During the course of processing beyond Step 199, additional data is then entered by the caregiver when prompted, based on observation or reasonable knowledge, and still further discrete data points are derived by the rules engine for completion of all aspects of the process. While at least one preferred embodiment processes the rules engine in an independent server with encrypted access, data from the embodiment's local table is preferably de-identified before being sent for processing in the rules engine server.

From initial Step 199, a series of query steps are executed, preferably presented in serial fashion, even though the logic of the corresponding rules engine has an arguably non-serial character. The successive queries serve to gather sufficient information and/or to verify information already on file in the facility's or network's EMR system 420, as gathered by the background process mentioned previously. The extent of information required to be gathered or verified is determined by the software rules, as may be customized for specific classes of users and/or specific users, although the sufficiency is based on the object of ultimately recommending and/or completing the ordering process for the relevant imaging procedure, to be described further below. While the absence of sufficient data may be characterized as a "Stop" or an "Uncertain" condition, preferred embodiments allow procession of other query steps despite the "Stop" or "Uncertain" conditions, although it should be understood that ultimate results cannot be reached without remedying such "Stop" or "Uncertain" conditions.

Implementation of the process described above is carried out through software driven query sessions involving the health care provider 490. The software provides evidence-based clinical information at the point of care. The rules engine associated with the software extracts patient data from a corresponding EMR system 420 (and/or comparable database or network of databases) and creates suggested orders for physicians 490 to consider in the management of heart and vascular disease (as an example). The patient care technician 490 will typically access a symptoms information window for each patient encounter by selecting a "Symptoms" tab on the system user template. The Symptoms window would include questions to ask the patient 500; the first may relate (for example) to claudication symptoms and the rest to sleep patterns (for example) or the like. If additional data is needed for any of the care paths, the Symptoms window will display a field to insert the missing data.

When the provider 490 opens the patient's home page 300 within the system 10, the rules engine 20 will have automatically processed the data entered and if orders are recommended, or if data entry is required by the provider 490, a color-coded indicator will appear on the home page 300. Selecting this indicator will launch the specific system approval template 370. Additionally, if there are orders recommended or data entry required, the provider 490 will be redirected automatically to the approval template 370 the first time they open an order plan template. There is also preferably a link provided on the order plan template that allows access to the approval template 370 at any time.

The approval template has a section for each of the active care paths. The criteria used to generate recommendations can be viewed by clicking the "Criteria" links in each care path section or on the care path window templates (the NUC for example). If any orders are recommended, a brief description of the order will be provided in an action field, the status will be "Waiting Review" and there will be the opportunity to select either "Approve" or "Decline" the order for each care path. Some care paths may be slightly different as they do not suggest any order actions and instead provide a recommendation for patient care considerations. Alternate wording for "Accept" or "Decline" such as "Approve" and "Ignore," respectively, may be used for the care path buttons of the approval template. Any other word or words with similar meanings may be substituted in order to give the provider 490 an opportunity to make a decision regarding the care path.

The provider 490 can "Accept" or "Decline" the recommendation as appropriate. Accepting an action will automatically add the recommended orders to the patient's order plan for the encounter. Once an order has been accepted and entered, the "Accept" and "Decline" selections will no longer be displayed for that care path. An indicator of the order status will show on the corresponding care path section on the system template. When an order is declined, the system will prompt the provider 490 for a reason with a data input window. The NUC care path (as an example) provides two ways to decline an order: "Decline" and "Exclude". The "Exclude" selection also declines the order, but will display a data input window with choices to describe why the patient 500 is being excluded from being processed by the care path. Selecting one of these choices will mark the patient's record with an absolute exclusion so the care path will not process on following patient visits. The provider 490 can also enter absolute exclusions by opening the appropriate care path template window and selecting one of the exclusions listed. If the provider 490 chooses to return to the order plan as a manner of leaving the Approval template, without either accepting or declining all of the recommended actions, they will be alerted that they will not be able to finalize and submit through the checkout template until all the outstanding suggested orders are addressed. All of the assessments need to be addressed before the provider 490 will be able to finalize the encounter.

The Approval template provides access to the care path template windows by selecting the "Launch" link provided. Once launched, the NUC care path may (for example) require the provider 490 to answer questions about the patient's current status. If any specific data is required from the provider 490, the software system then opens a query window that allows the provider 490 to answer the question with a single step. Processing continues automatically as the provider 490 answers the various queries presented. For example, the first question a provider 490 may be required to answer is if the patient 500 is on optimal tolerated medical therapy. If this question is answered "Yes" the patient's record will be flagged and the question will not be asked in future visits. Correspondingly, the result of this answer will be a data element within EMR system 420 which is accessible to system 10 for possible data extraction relating to future patient encounters. If it is answered "No" the question will be asked again if appropriate.

A further detail question that the provider 490 may need to answer to complete the processing of the NUC care path is the patient's NYHA class. The system 10 will check the NYHA Class field on the vital signs template and only prompt the provider 490 for an answer if there is nothing entered in the field for the current encounter. Again, when an answer is selected, the care path will automatically continue processing. The NYHA Class query window will typically require documentation for each patient visit so that the care path system has the data to complete processing. In addition, the system provides (through a selectable information button on the software display) further information regarding the NYHA Class criteria.

As a further example of the decision making operation of the system, if the provider 490 believes that the most recent Echo test provided a reliable left ventricular ejection fraction (LVEF) measurement, then the selection tree set forth in the flowchart of FIGS. 3-4 may be launched. As part of this process, the provider 490 may select an EF history link to bring up a list of the patient's previous LVEF measurements. When a new LVEF value is selected from the list, the care path will automatically reprocess using the new value and may alter the suggested order based on the new information. As described above, system 10 may incorporate past and presently determined LVEF measurements into an easily understood display (e.g., a graphical display over time) presented on GUI 300. This display is intended to be indicative of the progress of the condition of patient 500 over time, whether that progress is improving, declining, or some other trend. Accordingly, the easily observable and understandable display within the output of system 10 will help determine whether nuclear imaging is appropriate and recommended for a particular patient 500.

Alternative embodiments of certain aspects of the present invention also include adaptations of the methods and systems described above, such as adaptations to be used for providing a straightforward method and system by which a healthcare professional can determine whether, when, and how any particular type of test or medical procedure is indicated for any particular patient 500, or for any patient 500 of a particular class of patients. Such alternatives include comparable adaptations such that adoption of the test or procedure will likely be accelerated among health care providers who are not intimately familiar with the health care issue being addressed or the process involved. While the various particular steps that would be useful in determining whether a patient 500 is suited for a procedure will vary depending on the specific procedure, it will be evident to those of skill in the art whether and how systems and methods of the present method can be adapted for use with any particular procedures, or groups thereof.

Specific details are given in the above description to provide a thorough understanding of various preferred embodiments. However, it is understood that these and other embodiments may be practiced without these specific details. For example, circuits or processes may be shown in block diagrams in order not to obscure the embodiments in unnecessary detail. In other instances, well-known processes, algorithms, structures, and techniques may be shown without unnecessary detail in order to avoid obscuring the embodiments.

Implementation of the techniques, blocks, steps, and means described above may be done in various ways. For example, these techniques, blocks, steps, and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be rearranged. A process is terminated when its operations are completed, but could have many additional steps not included in the figure. A process may correspond to a method, a function, a procedure, a subroutine, a subprogram, etc. When a process corresponds to a function, its termination corresponds to a return of the function to the calling function or the main function.

Embodiments of the invention may involve use of a portable user interface that is adapted to provide or allow continuous or intermittent secure links with the facility network 400. For a middleware and/or other software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor and may be downloadable through an internet connection service. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to, portable or fixed storage devices, optical storage devices, wireless channels, and/or various other storage mediums capable of storing that contain or carry instruction(s) and/or data.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

While the principles of the disclosure have been described above in connection with specific apparatuses and methods, it is to be clearly understood that this description is made only by way of example and not as limitation on the scope of the disclosure. Whether now known or later discovered, there are countless other alternatives, variations, and modifications of the many features of the various described and illustrated embodiments, both in the process and in the system characteristics, that will be evident to those of skill in the art after careful and discerning review of the foregoing descriptions, particularly if they are also able to review all of the various systems and methods that have been tried in the public domain or otherwise described in the prior art. All such alternatives, variations, and modifications are contemplated to fall within the scope of the present invention.

Although the present invention has been described in terms of the foregoing preferred and alternative embodiments, these descriptions and embodiments have been provided by way of explanation of examples only, in order to facilitate understanding of the present invention. As such, the descriptions and embodiments are not to be construed as limiting the present invention, the scope of which is limited only by the claims of this and any related patent applications and any amendments thereto.

In alternative embodiments, by providing a reliable risk management system for nuclear appropriateness determinations, the system is further adapted to also present the option to order interventions and/or consults to reduce the risk of cardiovascular disorders. A particularly preferred variation of this alternative embodiment automatically presents the option of ordering a specialty consult to assess whether Radio Frequency Ablation should be conducted whenever a patient 500 is at high risk on the FRS scoring system.

Due to the reliability of the NUC module, in still another alternative, the above described NUC module embodiments are integrated as part of an insurance management system that allows for precertification requirements and/or independent Radiology Review Boards, which both add an added layer of costs, to be deemed unnecessary whenever the NUC module concludes that the nuclear procedure is Appropriate. Such alternative still uses pre-cert and RRB measures as ordering options, but those ordering options are only presented when the conclusion is "uncertain." A particularly preferred approach involves an insurance management system that generally disallows nuclear imaging cost reimbursement for patients 500 at low risk FRS; while requiring additional pre-authorization measures (such as pre-cert and/or RRB requirements) for FRS values indicating patients 500 at moderate or intermediate risk; whereas patients 500 at high risk are exempt from additional preauthorization requirements. Because they give an indication of who is most likely to develop cardiovascular disease they also indicate who is most likely to benefit from prevention.

Many other alternatives will be evident to those of skill in the art in light of this description.

The invention claimed is:

1. An improved healthcare facility for providing patient care, said improved healthcare facility having improvements to result in improved operating efficiency and reduced operating costs for said healthcare facility, said improved healthcare facility comprising:
   a) a healthcare facility network having a data management system comprising an EMR data management system that is adapted to store electronic medical records (EMR) of patients;
   b) one or more secure terminals each having a display, said one or more secure terminals being in network communication with said EMR data management system;
   c) identifiable memory locations for storing discrete data elements;
   d) data processors associated with said one or more secure terminals;
   e) a programmed middleware system being integrated with said EMR data management system, wherein interaction by a user with said programmed middleware system occurs within a user interface of said EMR data management system;
   f) a nuclear medical imaging device being located in said healthcare facility, said nuclear medical imaging device comprising a surface for accepting and positioning a patient for performing a nuclear imaging procedure and one or more image capture devices positioned to capture images of a particular patient;
   g) an authorization system associated with said nuclear medical imaging device for authorizing use of said nuclear imaging device, said authorization system being in network communication with said programmed middleware system, said authorization system being adapted to electronically disable use of said nuclear medical imaging device until an authorization signal is received from said programmed middleware system;
   h) said authorization system further being configured for receiving a data signal from said programmed middleware system wherein said signal is an authorization to use said nuclear medical imaging device, and wherein said authorization system electronically enables operation of said nuclear medical imaging device for performing nuclear imaging on said particular patient;
   i) said programmed middleware system being adapted to securely access EMR data stored by said EMR data management system, wherein said programmed middleware system extracts said EMR data relating to said particular patient, said EMR data being all forms of data which are relevant to a particular condition of said particular patient, said forms of data comprising structured data, free-text data, and image data;
   j) said programmed middleware system being configured to operate through a graphic user interface having regions which allow an authorized user of said programmed middleware system to interact with said data management system of said healthcare facility network, said regions comprising graphical components including graphical fields, toolbars, and windows;
   k) said programmed middleware system being adapted to convey an identification of said particular patient from said EMR data management system to said one or more secure terminals, said particular patient being a patient who is enrolled for receiving care through said healthcare facility network;
   l) said programmed middleware system being programmed to electronically access a data file in said EMR data management system corresponding to the patient identification conveyed to said one or more secure terminals;
   m) said programmed middleware system automatically formatting discrete data elements corresponding to data electronically accessed from said data file, said discrete data elements comprising EMR data extracted from said EMR data management system, said automatic formatting including normalizing said extracted EMR data into a usable format for use by said programmed middleware system;
   n) said discrete data elements comprising a plurality of date data entries, said plurality of date data entries including entries that correspond to the respective most recent dates of one or more cardiac procedures performed in relation to said particular patient;
   o) said programmed middleware system being programmed to apply rules for determining an appropriate care path for said particular patient, wherein said rules, wherein said rules:
      1) relate to comparisons of said plurality of date data entries of said cardiac procedures;
      2) relate to comparisons of a value of one or more types of cardiac risk scores; and 3) incorporate, at least in part, standards established in published clinical guidelines relating to cardiovascular conditions;

p) upon determining said appropriate care path for said particular patient, said programmed middleware system causing said one or more secure terminals to present a screen bearing an option for injecting a new Nuclear Imaging Procedure (NIP) order for said particular patient into said EMR data management system, wherein said NIP order requires authorization before the new nuclear imaging order is sent;

q) said programmed middleware system being programmed to cause said one or more secure terminals to display said NIP order to a caregiver, the displayed order including particulars corresponding to a nuclear imaging procedure order template;

r) said programmed middleware system being further programmed to cause said data processors associated with said one or more secure terminals to automatically populate the particulars of the nuclear imaging order template with patient data corresponding to an identification of said particular patient and with variable data corresponding to said formatted extracted EMR data; and s) said programmed middleware system being further programmed to input information on said NIP order template, said information corresponding to details regarding one or more reasons said NIP order is being injected through said EMR data management system as being necessary for said particular patient, wherein said details are formulated to at least conform to published clinical guidelines.

2. The improved healthcare facility of claim 1, wherein said one or more cardiac procedures include any Percutaneous Coronary Intervention (PCI), Myocardial Perfusion Imaging (MPI), and/or Cardiac Catheterization (CATH) performed in relation to said particular patient.

3. The improved healthcare facility of claim 2, wherein said one or more secure terminals are adapted to present a plurality of order options to a caregiver, said plurality of order options including a NIP ordering option.

4. The improved healthcare facility of claim 3, wherein said rules are applied by said programmed middleware system, wherein:

a) said programmed middleware system determines from said discrete data elements a date data entry, if any, that corresponds to a date of a most recent cardiac procedure performed in relation to said particular patient;

b) said programmed middleware system being programmed such that, if the date of the most recent cardiac procedure of any corresponding date data entry determined by said programmed middleware system is within a two-year span preceding a current date, then said programmed middleware system immediately prompts the caregiver that a new order for nuclear imaging is inappropriate, and wherein said programmed middleware system does not initiate a new order for nuclear imaging;

c) said programmed middleware system being programmed such that, if the date of the most recent cardiac procedure of any corresponding date data entry determined by said programmed middleware system is not within the two-year span preceding the current date, the programmed middleware system then:

1) determines from said discrete data elements a date data entry, if any, that corresponds to a most recent Coronary Artery Bypass Graft (CABG) performed in relation to said particular patient; and 2) if the date of the most recent CABG of any corresponding date data entry determined by said programmed middleware system is within a five-year span preceding the current date, the programmed middleware system then:

(i) determines whether the date of the most recent cardiac procedure of any corresponding date data entry of the most recent cardiac procedure is more recent than the date of the most recent CABG of any corresponding date data entry determined by said programmed middleware system; and (ii) if the determination made by said programmed middleware system is that the date of the most recent cardiac procedure is more recent than the date of the most recent CABG, then said programmed middleware system does not initiate a new order for nuclear imaging; and d) said programmed middleware system being further programmed such that, if all requisite determinations are completed, such that the date of the most recent cardiac procedure of any corresponding date data entry determined by said programmed middleware system is not within the two-year span preceding the current date, and such that one of the following determinations is made by said programmed middleware system: (1) the date of the most recent CABG of any corresponding date data entry determined by said programmed middleware system is not within a five-year span preceding the current date, or (2) wherein the date of the most recent CABG of any corresponding date data entry determined by said programmed middleware system is within a five-year span preceding the current date but the date of the most recent cardiac procedure is not more recent than the date of the most recent CABG, then said programmed middleware system causes said one or more secure terminals to present a screen bearing an option for sending a new Nuclear Imaging Procedure (NIP) order for said particular patient (for reference, a "NIP order sending option"), said NIP order sending option requiring authorization before the new nuclear imaging order is implemented.

5. The improved healthcare facility of claim 4, wherein said displayed order includes an order for a PCI procedure for said particular patient identified by said programmed middleware system.

6. The improved healthcare facility of claim 4, wherein said programmed middleware system is further programmed to:

a) mine said EMR to compile data files corresponding to patients enrolled for care through said healthcare facility network, the compiled data files including said data file accessed by said programmed middleware system for said particular patient; and b) store the compiled files from mining said EMR in a database separate from said EMR of said data management system.

7. The improved healthcare facility of claim 4, wherein:

a) said programmed middleware system determines whether the date of the most recent PCI procedure is more recent than the date of the most recent CABG procedure and, if so, then determining whether the date of the most recent MPI procedure is more recent than the date of the most recent CABG procedure for said particular patient; and b) if said programmed middleware system determines that the date of the most recent MPI procedure is more recent than the date of the most recent CABG procedure, then said programmed middleware system being further programmed to not initiate a new order for nuclear imaging.

8. The improved healthcare facility of claim 7, wherein said programmed middleware system is programmed to:
a) determine a first cardiovascular risk score for said particular patient, said programmed middleware system using a first cardiovascular risk scoring system that is reflective of the patient's risk of developing cardiovascular disease, said first cardiovascular risk scoring system being based on data obtained from the Framingham Heart Study;
b) determine a second cardiovascular risk score for said particular patient, said programmed middleware system using a second cardiovascular risk scoring system that is also reflective of the patient's risk of developing cardiovascular disease;
c) said second cardiovascular risk scoring system being more related to coronary calcification than the first cardiovascular risk scoring system; and
d) said programmed middleware system being further programmed such that, if one or both of said first and second cardiovascular risk scores are determined by said programmed middleware system to not be reflective of high risk for said particular patient developing cardiovascular disease, then said programmed middleware system does not initiate a new order for nuclear imaging.

9. The improved healthcare facility of claim 7, wherein said programmed middleware system is programmed to:
a) determine the most recent Framingham Risk Score for said particular patient and the date when said most recent Framingham Risk score was determined;
b) determine the most recent Agatston score for said particular patient and the date when said Agatston score was determined; and
c) said programmed middleware system being further programmed such that, if either or both of said most recent Framingham Risk Score and said most recent Agatston Score are determined to not be reflective of high risk for said particular patient developing cardiovascular disease, then said programmed middleware system does not initiate a new order for nuclear imaging; and
d) if said most recent Framingham Risk Score is not reflective of high risk for said particular patient developing cardiovascular disease over a ten-year period, and if the most recent MPI date for said particular patient is more recent than or equal to said Agatston date, then said programmed middleware system does not initiate an order for a new nuclear imaging procedure.

10. The improved healthcare facility of claim 9, wherein said programmed middleware system is programmed to:
a) cause said one or more secure terminals to prompt the caregiver to provide and/or confirm patient data of the type used for calculating Agatston Risk Scores;
b) cause said one or more secure terminals to prompt the caregiver to provide and/or confirm patient data of the type used for calculating Framingham Risk Scores;
c) calculate an Agatston Risk Score and a Framingham Risk Score for said particular patient based in part on the data file corresponding to said particular patient and based in part on data input provided through said one or more secure terminals;
d) determine whether said Agatston Risk Score predicts a high risk of cardiovascular disease for said particular patient;
e) determine whether said Framingham Risk Score predicts a high risk of cardiovascular disease for said particular patient; and
f) said programmed middleware system being further programmed such that, if either said Agatston Risk Score or said Framingham Risk Score predicts a high risk of cardiovascular disease for said particular patient, then said programmed middleware system does not initiate an order for a new nuclear imaging procedure.

11. The improved healthcare facility of claim 10, wherein said programmed middleware system is programmed to:
a) determine from said data file a date data entry that corresponds to a date of a most recent CATH procedure, if any, performed in relation to said particular patient;
b) said programmed middleware system being further programmed such that:
1) if a most recent CATH date for said particular patient, as determined by said programmed middleware system, is more recent than or equal to the most recent Agatston date, then said programmed middleware system does not initiate a new order for nuclear imaging;
2) said programmed middleware system further determines whether the date of the most recent MPI procedure, as determined by said programmed middleware system, is greater than or equal to said most recent Agatston score date, and said programmed middleware system determines whether the most recent CATH date is greater than or equal to said most recent score date;
3) if either said MPI date or said CATH date is more recent as determined by said programmed middleware system, then said programmed middleware system determines if said most recent Framingham Risk Score predicts a medium risk of cardiovascular disease for said particular patient, and said programmed middleware system determines whether said most recent Framingham Risk Score predicts a high risk of cardiovascular disease for said particular patient;
4) if said most recent Framingham Risk score predicts a high risk of cardiovascular disease for said particular patient, then said programmed middleware system does not initiate an order for a new nuclear imaging procedure; and
5) if either said most recent Agatston Score or said most recent Framingham Risk Score predicts a high risk of cardiovascular disease for said particular patient, then said programmed middleware system does not initiate an order for a new nuclear imaging procedure.

12. The improved healthcare facility of claim 9, said programmed middleware system is programmed to:
a) cause said one or more secure terminals to prompt the caregiver to provide and/or confirm patient data of the type used for calculating Framingham Risk Scores;
b) calculate a Framingham Risk Score for said particular patient based in part on the data file corresponding to said particular patient and based in part on data input provided through said one or more secure terminals;

c) determine whether said Framingham Risk Score is High; and d) said programmed middleware system being further programmed such that, if said Framingham Risk Score is determined to be High, then said programmed middleware system does not initiate an order for a new nuclear imaging procedure.

13. The improved healthcare facility of claim 12, wherein said programmed middleware system is programmed such that:

a) if the determination by the programmed middleware system is not that the last MPI date is greater than or equal to the date of the last Agatston Score or whether the last CATH date is greater than or equal to the date of the last Agatston Score, then said programmed middleware system determines if the patient's Framingham Risk Score is Medium;

b) if the determination made by the programmed middleware system is that the patient's Framingham Risk Score is Medium, then the programmed middleware system determines if the Agatston date is defined and if the Agatston Score is greater than 400;

c) if the determination by the programmed middleware system is that the Agatston date is defined and Agatston Score is greater than 400, then the programmed middleware system does not initiate an order for a new nuclear imaging procedure;

d) if the determination by the programmed middleware system is not that the Agatston date is defined and the Agatston Score is greater than 400, then the programmed middleware system determines if the Agatston date is defined and if the Agatston Score is greater than or equal to 100;

e) if the determination by the programmed middleware system is that the Agatston date is defined and the Agatston Score is greater than or equal to 100, then the programmed middleware system does not initiate an order for a new nuclear imaging procedure;

f) if the determination by the programmed middleware system is not that the Agatston date is defined and the Agatston Score is greater than or equal to 100, then the programmed middleware system does not initiate an order for a new nuclear imaging procedure;

g) if the determination by the programmed middleware system is not that the patient's Framingham Risk Score is Medium, then the programmed middleware system determines if the Agatston date is defined;

h) if the determination by the programmed middleware system is that the Agatston date is defined, then the programmed middleware system determines if the Agatston Score is greater than 400;

i) if the determination by the programmed middleware system is that the Agatston Score is greater than 400, then the programmed middleware system does not proceed with any further determinations as the patient is appropriate for MPI;

j) if the determination by the programmed middleware system is not that the Agatston Score is greater than 400, then the programmed middleware system determines if the Agatston Score is greater than or equal to 100;

k) if the determination by the programmed middleware system is that the Agatston Score is greater than or equal to 100, then the programmed middleware system does not proceed with any further determinations as the patient is uncertain for MPI; and l) if the determination by the programmed middleware system is not that the Agatston Score is greater than or equal to 100, then the programmed middleware system does not initiate a new order for nuclear imaging.

14. An improved healthcare facility for providing patient care, said improved healthcare facility having improvements to result in improved operating efficiency and reduced operating costs for said healthcare facility, said improved healthcare facility comprising:

a) a healthcare facility network having a data management system comprising an EMR data management system that is adapted to store electronic medical records (EMR) of patients;

b) one or more secure terminals each having a display, said one or more secure terminals being in network communication with said EMR data management system;

c) identifiable memory locations for storing discrete data elements;

d) data processors associated with said one or more secure terminals;

e) a programmed middleware system being integrated with said EMR data management system, wherein interaction by a user of said programmed middleware system occurs within said EMR data management system;

f) a nuclear medical imaging device being located in said healthcare facility, said nuclear medical imaging device being operable to capture images of a particular patient;

g) an authorization system associated with said nuclear medical imaging device for authorizing use of said nuclear imaging device, said authorization system being in network communication with said programmed middleware system wherein said authorization system is configured for disabling use of said nuclear medical imaging device;

h) said authorization system further being configured for receiving a data signal from said programmed middleware system wherein said signal is an authorization to use said nuclear medical imaging device, and wherein said authorization system enables operation of said nuclear medical imaging device;

i) said programmed middleware system being adapted to securely access EMR data stored by said EMR data management system, wherein said programmed middleware system extracts said EMR data relating to said particular patient, said EMR data being all forms of data which are relevant to a particular condition of said particular patient, wherein said forms of data comprise structured data, free-text data, and image data;

j) said programmed middleware system being adapted to create readily executable ordering options associated with nuclear imaging options for said particular patient;

k) said programmed middleware system being configured to operate through a graphic user interface having regions which allow an authorized user of said programmed middleware system to interact with said data management system of said healthcare facility network, said regions comprising graphical components including graphical fields, toolbars, and windows;

l) said programmed middleware system being adapted to convey an identification of said particular patient from said EMR data management system to said one or more secure terminals, said particular patient being a patient who is enrolled for receiving care through said healthcare facility network;

m) said programmed middleware system being programmed to electronically access a data file in said EMR data management system corresponding to the patient identification conveyed to said one or more secure terminals;

n) said programmed middleware system automatically formatting discrete data elements corresponding to data electronically accessed from said data file, wherein said discrete data elements comprise EMR data extracted from said EMR data management system, wherein said automatic formatting comprises normalizing said extracted EMR data into a usable format for use with said computer-based ordering system;

o) said programmed middleware system being further programmed to automatically store said discrete data elements in said identifiable memory location;

p) said programmed middleware system being further programmed to automatically update said discrete data elements stored in said identifiable memory locations, whereby said discrete data elements are automatically verified;

q) said programmed middleware system being further programmed to determine from said extracted EMR data a plurality of date data entries, said plurality of date data entries including entries that correspond to the respective most recent dates of multiple types of cardiac procedures performed in relation to said particular patient;

r) said programmed middleware system being further programmed such that, if the date of the most recent cardiac procedure of any corresponding date data entry determined by said programmed middleware system is within a two-year span preceding a current date, then said programmed middleware system immediately prompts a caregiver that a new order for nuclear imaging is inappropriate, and said programmed middleware system does not initiate a new order for nuclear imaging;

s) said programmed middleware system being further programmed such that, if the date of the most recent cardiac procedure of any corresponding date data entry determined by said programmed middleware system is not within the two-year span preceding the current date, the programmed middleware system then:
1) determines from said discrete data elements a date data entry, if any, that corresponds to a most recent Coronary Artery Bypass Graft (CABG) performed in relation to said particular patient; and
2) if the date of the most recent CABG of any corresponding date data entry determined by said programmed middleware system is within a five-year span preceding the current date, the programmed middleware system then:
(i) determines whether the date of the most recent cardiac procedure of any corresponding date data entry of the most recent cardiac procedure is more recent than the date of the most recent CABG of any corresponding date data entry determined by said programmed middleware system; and
(ii) if the determination made by said programmed middleware system is that the date of the most recent cardiac procedure is more recent than the date of the most recent CABG, then the programmed middleware system does not initiate a new order for nuclear imaging; and t) said programmed middleware system being further programmed such that, if all requisite determinations are completed, such that the date of the most recent cardiac procedure of any corresponding date data entry determined by said programmed middleware system is not within the two-year span preceding the current date, and such that one of the following determinations is made by said programmed middleware system: (1) the date of the most recent CABG of any corresponding date data entry determined by said programmed middleware system is not within a five-year span preceding the current date, or (2) wherein the date of the most recent CABG of any corresponding date data entry determined by said programmed middleware system is within a five-year span preceding the current date but the date of the most recent cardiac procedure is not more recent than the date of the most recent CABG, then said programmed middleware system causes the point of care electronic caregiver terminal to present a screen bearing an option for sending a new Nuclear Imaging Procedure (NIP) order for said particular patient (for reference, a "NIP order sending option"), said NIP order sending option requiring authorization before the new nuclear imaging order is sent;

u) said programmed middleware system being further programmed to cause said one or more secure terminals to display said NIP order to said caregiver, the displayed order including particulars corresponding to a nuclear imaging procedure order template;

v) said programmed middleware system being further programmed to cause said data processors associated with said one or more secure terminals to automatically populate the particulars of the nuclear imaging order template with patient data corresponding to an identification of said particular patient and with variable data corresponding to said formatted extracted EMR data; and w) said programmed middleware system being further programmed to input on said NIP order template information corresponding to details regarding why said NIP order is being injected through said EMR data management system as being necessary for said particular patient, wherein said details are formulated to at least conform to current published clinical guidelines.

* * * * *